United States Patent [19]

Jörgensen et al.

[11] Patent Number: 5,293,838

[45] Date of Patent: Mar. 15, 1994

[54] METHOD AND APPARATUS FOR INCUBATING EGGS AND LARVAE OF FISH CRUSTACEANS AND SIMILAR ORGANISMS

[76] Inventors: Leif Jörgensen, N-7022, Trondheim, Norway; Hans Grasdalen, N-7033, Trondheim, Norway

[21] Appl. No.: 648,989

[22] Filed: Jan. 31, 1991

Related U.S. Application Data

[63] Continuation-in-part of Ser. No. 215,521, Jul. 6, 1988, abandoned.

[30] Foreign Application Priority Data

Jul. 10, 1987 [NO] Norway .................................. 872869

[51] Int. Cl.$^5$ ...................... A01K 61/00; A01K 63/00
[52] U.S. Cl. .................................... 119/205; 119/218; 435/240.22; 435/260; 800/2
[58] Field of Search ............... 800/2; 435/260, 240.22; 119/2, 3

[56] References Cited

U.S. PATENT DOCUMENTS

| | | | |
|---|---|---|---|
| 4,214,551 | 7/1980 | McNeil et al. | 119/3 |
| 4,317,429 | 3/1982 | Leighton et al. | 119/2 |
| 4,615,883 | 10/1986 | Nelsen et al. | 424/84 |
| 4,647,536 | 3/1987 | Masbach et al. | 435/177 |
| 4,681,063 | 7/1987 | Hebrank | 119/6.8 |
| 4,702,921 | 10/1987 | Ueda | 426/48 |
| 4,798,786 | 1/1989 | Tice et al. | 435/177 |

FOREIGN PATENT DOCUMENTS 62-134067 6/1987 Japan .

OTHER PUBLICATIONS

White, M. L. 1960 J. Phys. Chem. 64, 1563–1565.
White et al., 1961. J. Polymer Sci. 55, 731–740.
Curtis, H. 1983, in: *Biology*, Fourth Edition, Worth Publ. Co. Inc. New York, N.Y. p. 534.
Berger et al., (eds.) 1987, in: *Methods Enzymol*, vol. 152, "*Guide to Molecular Cloning Techniques.*"p. 67, Academic Press, San Diego.

*Primary Examiner*—Christopher S. F. Low
*Attorney, Agent, or Firm*—Dennison, Meserole, Pollack & Scheiner

[57] ABSTRACT

A method for incubating eggs or larvae of fish, crustaceans, or related organisms. The eggs or larvae are located in depressions in the surface of a plate formed of an aqueous polymeric gel, and the surface is sealingly covered with a porous membrane capable of gas transport therethrough. The plate sealed with the membrane is placed in at least intermittent contact with water during the incubation period, and the eggs or larvae are separated from the plate and membrane after incubation is complete.

16 Claims, 4 Drawing Sheets

METHOD AND APPARATUS FOR INCUBATING EGGS AND LARVAE OF FISH CRUSTACEANS AND SIMILAR ORGANISMS

This application is a continuation-in-part of U.S. patent application Ser. No. 07/215,521, filed Jul. 6, 1988, now abandoned.

BACKGROUND OF THE INVENTION

1. Field of the Invention

This invention relates to the field of incubation of viable eggs and larvae of fish, crustaceans and similar organisms.

2. DESCRIPTION OF RELATED ART

When traditional incubation methods are used, the fatality rate among eggs and larvae is high due to impact and other mechanical forces. This is a problem for both pelagic (freely-suspended) and demersal (seal bottom resident) fish eggs.

Certain types of larvae are extremely sensitive to mechanical forces. This is particularly the case for halibut, where the incubation of the larvae prior to the start of feeding seems to be a problem for the production of fry.

In some situations, traditional approaches necessitate keeping the salinity of the water at a high level to prevent the eggs and larvae from sinking to the bottom. From an energy perspective, it would have been more rational to incubate eggs or larvae at lower salinity levels, since these organisms will then use less energy for ion-control.

Another substantial problem with traditional incubation systems is that eggs/larvae are very exposed to fungal and bacterial infection.

A further difficulty with present systems is the maintenance of eggs/larvae during vaccination and gene transfer. This is a factor which makes such treatment difficult to implement on a commercial scale.

SUMMARY OF THE INVENTION

The primary object of the invention is the incubation of eggs/larvae of fish and crustaceans, where the eggs/larvae are protected as much as possible from physical forces such as impact and blows.

A further object of the invention is to prevent the organisms in question from coming into contact with fungi, viruses, and bacteria, and to immobilize the organisms so as to allow injection and vaccination.

It is another object of the invention to provide a method and apparatus allowing eggs or larvae to be transported for longer distances, without liberating the eggs/larvae from their safe incubation environment.

These objects are achieved by encapsulating and thereby immobilizing the eggs in a gel material, in which the gel material protects the eggs/larvae from external mechanical influence. Further, the nature of the gel ensures sufficient oxygen supply, and transport of excretory material including $CO_2$ and $NH_3$ away from the egg/larvae.

One method for incubating eggs comprises locating the eggs into cavities (gel chambers) in a gel plate (similar to an egg tray), whereupon a membrane is laid upon the plate, covering the entire plate and all gel chambers containing the eggs and establishing a tight seal. The seal should be so tight that there is no possibility for either air or liquid to flow between the gel chambers, or through the sides between the membrane and gel plate, thereby providing sterile surroundings during the incubation. Moreover, the eggs should be disinfected before being transferred to the respective gel chambers.

The plates may comprise a dissolvable gel material, whereupon the eggs are cast into the plate in one step. When the incubation is complete, the gel material may be dissolved by, for example, flushing away the components interconnecting the gel with, for example, water, $NaH_2PO_4$ or monovalent ions, this dissolving process requiring a relatively long period of time. Some gels can also be removed by temperature change.

The plates can alternatively be made of a relatively rigid material, such as polyacrylamide gel (hereinafter referred to as PAAm gel). The plates are then cast in advance with the desired shape, dimensions and number of gel chambers by using a mold having an inverse geometry to the plate. In case of a PAAm gel, the resulting plate is thereafter washed in order to remove any unreacted monomer remaining in the gel. Then, the eggs are located into their respective gel chambers, and finally the gel chambers are completely covered and closed by applying a membrane on the plate. It is important that the plates be cast with smooth and planar surfaces in order to ensure a sufficient seal between the plate and the membrane.

The membrane may be composed of the same material as the plate itself, but in which the thickness of the membrane is small enough to ensure a sufficient flow of oxygen from the surroundings into the gel chambers and excretory material ($CO_2$, $NH_3$) away from the gel chambers. In order to provide a tight seal between the respective gel chambers and the surroundings, fixing plates are applied to both sides of the incubation plate. The plate, now conforming to the membrane, has in advance been perforated in such a way that the respective gel chambers are allowed to communicate with the surroundings through the membrane. The oppositely disposed fixing plates are held together by means of clamps, screws, bolts or the like. When the incubation is complete, the larvae are uncovered and released by simply mechanically separating the membrane from the plate.

In case of a PAAm gel, it is not possible to cast the plate with the eggs in one step, because the poisonous raw materials present in the mixture before polymerization will kill the eggs. However, one step processes are possible with certain dissolvable gel formers.

Thus a further method for incubating eggs comprises encapsulating the eggs in spherical capsules comprising a dissolvable gel material. If an alginate is used as a gel material, the eggs are first stirred into an alginate solution having a predetermined consistency, in which the resulting mixture then is dripped through a pipe, hose or the like, into a bath containing $CaCl_2$ in order to harden the gel material. This method results in nearly spherical capsules, although the term "spheres" as used herein also applies to capsules having other geometries, such as elliptical. When the larvae are evolved, the larvae may under certain circumstances escape from the gel independently, or the gel may be dissolved by exchanging the ions interconnecting the gel.

DETAILED DESCRIPTION OF THE INVENTION

Figure 1:
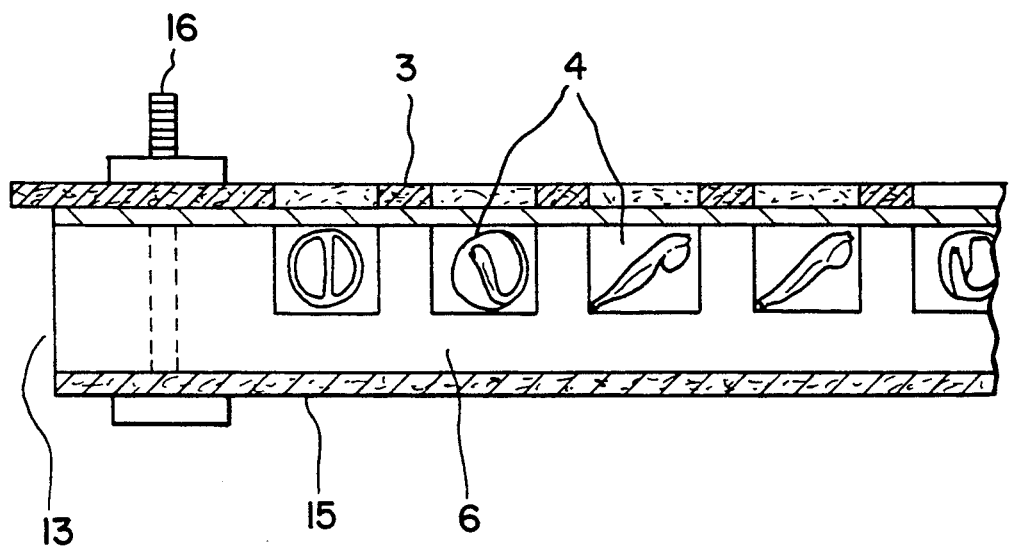
FIG. 1 shows in cross-section a plate for incubating eggs and larvae in accordance with the invention.

Two different gel forming materials are preferred for the invention, polyacrylamide and alginate. However, other gel forming materials may also be utilized, such as kappacarrageenan, and Instacryl-L ® and Instacryl H ® (registered Trademarks of Kodak International Biotechnologies, Inc. Conn.).

In the following methods for production of the gel materials, physical properties of the materials, and methods for incubating eggs in accordance with the present invention as described.

PAAm Gel, Production and Properties

This gel is made up of four different components, acrylamide (hereinafter referred to as AAm), methylene bis-acrylamide (hereinafter referred to as bis-AAm), ammonium persulphate and tetramethylethylenediamine (the latter hereinafter referred to as TEMED). Methylene bis-acrylamide acts as a cross-linking agent for the polymer, and accordingly affects strength and pore size of the final gel. The desired concentration of AAm may for example be provided by diluting a parent solution with distilled water. This parent solution comprising AAm and bis-AAm should be stored in dark surroundings. Then, TEMED is added to the solution, whereupon an inert gas such as nitrogen is bubbled through the solution for about 5 minutes. Ammonium sulphate is then added to the solution, and the gel polymerizes and hardens over a period of a few minutes, depending on various factors such as concentration, temperature, and oxygen level. Moreover, the solution may be sterilized by autoclaving before hardening.

The concentration of AAm in the starting solution is from about 5 to about 10% by weight, based upon the weight of the water; the concentration of bis-AAm is about 5% by weight of the total amount of AAm; and the concentration of TEMED constitutes about 0.5 ml/liter based upon the starting solution comprising all four components. In order to allow gel formation to occur, the minimal amount of monomer in such a mixture is about 2.5% by weight. If the concentration of AAm is less than 5%, the resulting gel will exhibit a consistency which is too loose to be regarded as practically usable, and if the concentration of AAm is more than 10%, the resulting gel will exhibit a too rigid and brittle consistency resulting in a reduction of the water permeability of the gel.

The average pore radius in gels containing a 5-10% AAm by weight with respect to water, is 1.2-1.8 nm. Accordingly, the pore diameter is 2.4-3.6 nm. The diameter of the water molecule is only 0.3 nm, while the smallest bacteria have a diameter of about $1 \times 10^{-6}$ m. Accordingly, water and other relatively small molecules can diffuse unhindered through the gel, whereas relatively large molecules and bacteria are prevented from entering the gel.

Alginate Gel

Gel materials for use with the present application may be produced by using a dissolvable alginate gel with an alginate content about 1 to 4% by weight. The gel is formed by simply dripping aqueous alginate solution into an aqueous solution containing nontoxic, stabilizing, divalent ions, e.g. $Ca^{2+}$, $Sr^{2+}$, $Ba^{2+}$, generally having a concentration between 0.1 and 1.0 moles/liter ($Mg^{2+}$ ions destablize the gel). The alginate may, before being added to this solution, be sterilized by autoclaving and intermixed with eggs for incubation, so that the eggs are completely surrounded by the alginate solution, whereupon the alginate gel including the encapsulated eggs hardens contacting a solution such as $CaCl_2$. The mechanism for this hardening is diffusion of $Ca^{2+}$ ions into the gel structure resulting in bonding the alginate chains together. Thus, the strength, pore size and the consistency of the resulting gel may be tailored by altering the concentration of $Ca^{2+}$ in the solution. Divalent ions may also be added to the surrounding medium during incubation to stabilize the gel.

Dissolution of the gel may be carried out by flushing/washing the ions interconnecting the gel away. If the surrounding medium has a low concentration of stabilizing ions, these interconnecting ions will diffuse out from the gel and into the surrounding medium, resulting in a decrease of the gel strength. If the surrounding medium for example is sea water, the $Na^+$ ions will replace the $Ca^{2+}$ ions in the gel, whereupon the gel strength gradually decreases because the Na-alginate is soluble in water, as opposed to Ca-alginate. Moreover, the addition of $Na^+$ and $PO_4^{-3}$ ions to the surrounding medium, such as with $NaH_2PO_4$, will dissolve the gel structure and release the eggs/larvae.

Some gel materials, such as agar, often require gel forming temperatures which would kill the eggs/larvae, and are accordingly not intended to be included in the term "dissolvable gel" as used herein.

The alginate gels can, like PAAm-gels, be utilized for casting of plates for incubation including membranes, although it is preferred to form gel capsules when alginate is used.

Kappa-carrageenan Gels

As mentioned above, kappa-carrageenan can also be utilized for incubation, both with respect to capsules and to plates. This type of gel is in principle produced by adding kappa-carrageenan, typically in a concentration of 1-3% by weight in distilled water, to the eggs for incubation, whereupon the resulting mixture is dripped or poured into an aqueous solution of gel stabilizing ions, typically $K^+$ in the form of KCl, in which the concentration of KCl is less than 0.2 moles/liter, depending on the desired gelling temperature. This procedure may be carried out at room temperature, or alternatively at lower temperatures. The gelling temperature is dependent on the concentration of KCl; the lower the concentration of KCl, the lower gelling temperature. However, this gel material requires a certain concentration of $K^+$ ions present during the incubation of the eggs, in order to stabilize the gel. Other gel stabilizing ions are $Cs^+$, $Rb^+$ and $NH_4^+$.

Carrageenan gels show marked hysteresis, dissolving at a temperature in the range of 5°-30° C., typically about 10° C., above the gelling temperature, a property not observed for alginate. However, the gel can also be dissolved without utilizing heat in the presence of $I^-$ ions, for example from LiI.

Thus, carrageenan gels are thermoreversible in the sense that they "melt" upon heating and reform in cooling. This is in contrast to gels made from alginate with divalent metal ions, which are stable up to the boiling point of water. Whether this is a qualitative difference between the two gelling systems or merely a quantitative difference within the temperature range accessible for investigation (0°–100° C.) is not clear. It is well known that gels of carrageenan become increasingly stronger as the temperature is lowered below their melting point. Temperature dependence of the modulus of rigidity is also a property of alginate gels, i.e. the modulus remains approximately constant until the temperature of rupture or dissolution is reached. Such temperature dependence is most easily explained by assuming that junctions are ruptured during compression, and that their strength decreases when the temperature is increased. A transition temperature for alginate above the boiling point of water may therefore exist, and it is interesting that in certain mixed gelling systems (pectin and gelatin) thermoreversible gels can be formed.

Membranes

When incubating eggs/larvae with the plate method in accordance with the invention, the membrane provides the substantial part of the mass transfer between the eggs/larvae and the surrounding medium outside the gel.

Gel membranes are produced by casting a reinforcing structure into the gel, for example in the shape of a net-like structure. In the gel forming process, the net-like structure and the gel formers (solution of monomers/polymers) are compressed in a mold including a lid positioned thereabove. The reinforcement is strongly preferred in order to ensure sufficient mechanical strength of the membrane. If the reinforcement is omitted, the resulting membrane will easily break apart in handling. When using a reinforcement the gel membranes can be constructed very thin, typically 1 mm, but the thickness may be greater. It is preferred that the thickness of the membrane should be as small as possible, but a practical range of thickness is from 1 to 3 mm. The thickness of the gel membrane should be small enough to provide a sufficient transport of excretory matter away from the eggs/larvae and of oxygen to the eggs/larvae. Accordingly, the lower limit of thickness is restricted by practical handling, i.e. the membrane should be thick enough simply to prevent the membrane from disintegrating or breaking apart.

The membranes can comprise the same gel material as the plates, i.e. for example PAAm gel, alginate gel, kappa carrageenan, or Instacryl-H or Instacryl-L.

Experiments utilizing different types of membrane filters available on the market have been carried out. Membranes from Schleiner & Schull comprise cellulosic nitrate or nylon having a pore diameter of $0.2 \times 10^{-6}$ and $0.45 \times 10^{-6}$ m, respectively. Moreover, experiments utilizing Nucleopore filters having a pore diameter of $8 \times 10$ m have been carried out. As explained in further detail below, the membranes available on the market do not seem to provide any benefits with respect to membranes comprising gel material. One advantage of gel material is the transparency, resulting in a convenient surveillance of the development of the eggs/larvae from outside the gel chamber. Moreover, production of the gel membranes is less expensive than use of the commercially available membranes.

Physical Properties of the Gels

The water permeability of the gel is a property which is assumed, to a certain extent, to constitute an important property since in the absence of water, the eggs will dry out and die. The water permeability of the gel can be evaluated by casting gel plates (a diameter of 63 mm) having a thickness of 1 to 7 mm. These plates are located upon a grating at the bottom of a water filled cylinder. The measurements are carried out at a constant liquid head of 1962 Pa.

Generally, the water flux through the gel is small at the actual experimental conditions. Depending on the type of the alginate gels examined, the water flux have been determined to be within the range of 0.06–1.32 $1/(m^2 \text{ hour})$. The water flux in 4% PAAm gel is determined to be 0.02 $1/(m^2 \cdot \text{hour})$. However, the uncertainty connected with those measurements is relatively high, because the volume changes measured are small and occur over a long period of time.

The water permeability of the membrane filters is substantially higher. Membranes from Schleiner & Schull have been tested in the same manner as those mentioned above, with the following results:

| | |
|---|---|
| BAS 83 (0.2 um): | 376 $1/(m^2 \cdot \text{hour})$ |
| Nytran NY 13N (0.45 um): | 405 $1/(m^2 \cdot \text{hour})$ |

Considering the great difference of water permeability between gel membranes and membrane filters available on the market, one might have concluded that membrane filters were totally superior to gel membranes with respect to incubation. However, this is not the case when considering mortality rates from hatching and incubation. There are no clear tendencies suggesting that one type of membrane is better than the other, but gel membranes are preferred because of their transparency and low cost.

The elasticity of the gel materials is measured by compressing gel cylinders with constant cross-section (a diameter of 14 mm and length of 20 mm) at a constant rate of 0.2 mm/sec. The relationship between force and length of deformation is recorded on a printer, and modulus of elasticity (the so-called G modulus) may be calculated from the initial angle of declination of the curve. The force required to compress the gel 1 mm ($P_1$ mm) is also recorded. The measurements are carried out by means of an instrument of the type "Stevens L.F.R.A. Texture Analyser". The results from three different types of gels are set forth in Table 1 below.

TABLE 1

| Gel Type | $F_{1mm}$ (gram) | G (kN/m$^2$) |
|---|---|---|
| 0.5% alginate*) | 5 | 12 |
| 4% alginate **) | 392 | 131 |
| 4% PAAm | 3 | 3 |

*)Protan LF 10/60
**)Protan LF 20/40 RB

The results from Table 1 show that a 4% alginate gel is substantially more rigid than a 0.5% alginate gel, whereas a 4% PAAm gel to some extent is more elastic than a 0.5% alginate gel.

One of the advantages of the PAAm gel compared with alginate gel is clearly apparent from Table 1.1. The table shows the results with respect to force required to compress the gel 1 mm, comparing fresh gels with gels stored in sea water in 190 days at 5° C.

TABLE 1.1

| Gel Type | $P_{1mm}$ (grams) Fresh Gel | $P_{1mm}$ (grams) Stored 190 Days |
|---|---|---|
| 1% alginate*) | 26 | 7 |

TABLE 1.1-continued

| Gel Type | $P_{1mm}$ (grams) Fresh Gel | $P_{1mm}$ (grams) Stored 190 Days |
|---|---|---|
| 2% alginate*) | 82 | 27 |
| 4% alginate*) | 374 | 106 |
| 4% PAAm | 3 | 4 |
| 7.5% PAAm | 18 | 19 |
| 15% PAAm | 68 | 73 |

*)Protan LF 10/60

From Table 1.1 it is apparent that the strength of the alginate gels is dramatically reduced after being stored in sea water, whereas the PAAm gels are not affected at all.

Moreover, the alginate gels were covered by a slime layer after storage, thereby indicating microbial activity. No such activity was observed for the PAAm gels.

The reason for the resulting decrease in strength for the alginate gels may be that the gel is destabilized as a result of a deficiency of calcium ions in the sea water resulting in removal of the calcium ions by diffusion in favor of sodium ions. The gel structure is interconnected by calcium ions, whereas sodium alginate is soluble in water. Another possible explanation for the decrease in gel strength may be enzymatic cutting of the alginate chains due to microbial activity. However, both of these disadvantages may be avoided by adding $CaCl_2$ to the water surrounding the gel, and by preventing microbial activity, such as by adding disinfecting agents. Such circumstances impose additional requirements for alginate gels, and accordingly, PAAm gels are preferred.

Incubation Techniques

Most of the experiments have been carried out with salmon and rainbow trout by means of the techniques involving plate incubation according to the invention.

a) Plate Incubation

For plate incubation both alginate gels and PAAm gels can be utilized, as stated above. Since PAAm gels are preferred for production of incubation plates, this gel material will primarily be described.

When the reaction mixture for production of PAAm gels is prepared (as described hereinabove), the mixture will polymerize and harden during a short period of time, i.e. a few minutes. Therefore, the reaction mixture should be poured into a suitable mold for casting incubation plates immediately. This mold should exhibit an inverse geometry to the desired plates. After the gel forming is complete, the cast plate should rest for a few hours before use, in order to ensure a complete polymerization, preferably in water in order to prevent the gel material from drying out. The final cast gel plate should be removed from the mold submerged in water, since this arrangement reduces the risk of breaking the plate in pieces. Thereafter, the gel plate should be stored in water, to which may be added components for preventing growth of microbes.

The plates can be produced with any dimension and arrangement of gel chambers, depending on the combination desired. The shape of the gel chambers can also be chosen freely, but semi-spherical shapes are preferred. Typical plates which often have been utilized for the experiments have a length of 14 cm and a width of 16 cm. The thickness of the plates can be varied, depending on the size and type of the eggs/larvae, typically from 1 to 1.5 cm. Moreover, the typical plates are provided with 54 gel chambers. The incubation plates can also be provided with gel chambers in opposite surfaces of the plates with membranes covering both surfaces. In order to increase the area available for mass transfer, i.e. transportation of excretory matter away from the gel chamber and oxygen into the gel chamber, it is possible to provide the plates with one or more gel chambers extending through the whole plate; the gel chamber then communicates with the surroundings from both sides of the incubation plate. In this case, membranes must be again applied to both sides of the plate. However, it is not necessary to extend the depression through the entire thickness of the plate, since the same effect can be achieved by extending the depression through most of the thickness, leaving only a thin gel portion, substantially of membrane thickness, between the depression and the opposite surfaces of the plate. Reinforcement of this portion of the plate may be necessary.

Casting the eggs directly into a PAAm gel before gel formation in one step is not possible because the reaction components are poisonous. After the polymerization reaction is completed, the gel is no longer poisonous, but the resulting gel should be thoroughly flushed in order to remove any remaining poisonous monomers.

The gel membranes are produced in the same manner and can comprise the same materials as the gel plate, as described hereinabove.

One of the advantages of the PAAm gel is that the PAAm gel may easily be cast into different shapes, and it is easy to achieve planar and smooth surfaces. This is an important aspect with respect to providing a sufficient seal between the membrane and the gel plate. Further, the resulting gel plates are homogenous and do not shrink during the gelling process.

In the method of incubation, gel plates and membranes are washed with water, preferably sterilized water, and may be by disinfected prior to the washing by means of a chlorine bleach. Then, the gel plates are cooled and located upon ice during the whole procedure until the plate arrangement has been mounted. In most cases, the gel and the membrane are irradiated with ultraviolet radiation for about 15 to 30 minutes before supplying the eggs into the gel chambers. Immediately before the sterilized eggs are supplied, the gel is preferably washed with sterilized water. The resulting water film located on the plate surface will simplify the "rolling" of eggs into their respective gel chambers. Moreover, the eggs should be entered in an environment as dark as possible When all eggs have been located in their respective gel chambers, one in each chamber (e.g. 54 eggs), the membrane(s) is applied onto the plate. In order to maintain a tight seal, the gel plate and the membrane or membranes are fixed together by means of a frame, a perforated plate or the like, for example, constructed of polyvinyl chloride, plexiglass or polycarbonate. However, transparent plates comprising polyvinyl chloride or plexiglass are the preferred materials, wherein a plate conforming to the membrane is perforated in such a way that the respective gel chambers are allowed to communicate with the surroundings through the membrane. The oppositely located fixing plates are held together by means of clamps, screws, bolts or the like. The plates should preferably be constructed of a plexiglass This arrangement is illustrated in FIG. 1.

Referring to FIG. 1, gel plate 6 comprises depressions forming gel chambers 4 containing the eggs, where the gel chambers communicate with the surroundings. A membrane 3 is applied to the gel plate 6, covering all gel chambers, and thereby providing a proper seal between the respective gel chambers and between the chambers and the surroundings, after fixing the plate/membrane with fixing plates 15 and bolts 16.

Figure 2:
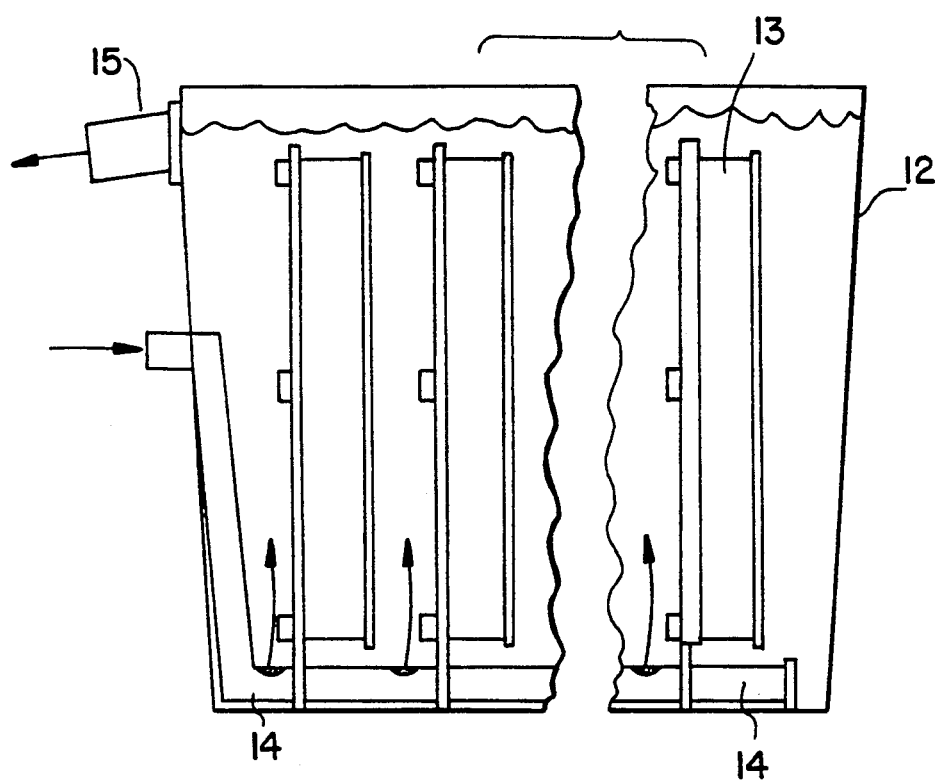
FIG. 2 shows a case including several plates according to FIG. 1 for incubating eggs and larvae in accordance with the invention.

Then, the complete incubation plates including the eggs are immediately transferred to incubating cases located in a dark cool room at a temperature generally between about 1°-10° C., depending on the species. An example of such a case is illustrated in FIG. 2. Each of the incubation cases 12, which in this example have outer dimensions 35×19×21 cm, can contain six incubation plates 13 as described above. The individual plates 13 are placed into the case in grooves or the like (not shown). The plates 13 can also be mounted in a horizontal manner, but a vertical arrangement of the layered plates is preferred. Below this plate arrangement, pipes, hoses, or the like 14 are located for distributing oxygen rich water into the case 12, preferably in an upwards direction in front of each plate 13. After a certain period of time, the supplied water exits the case 12 via an overflow pipe 15. If the plates were arranged in a horizontal manner, the distributor pipes 14 would have to be positioned in a substantially vertical direction, thereby distributing water in a horizontal direction between the individual plates 13.

Figure 4:
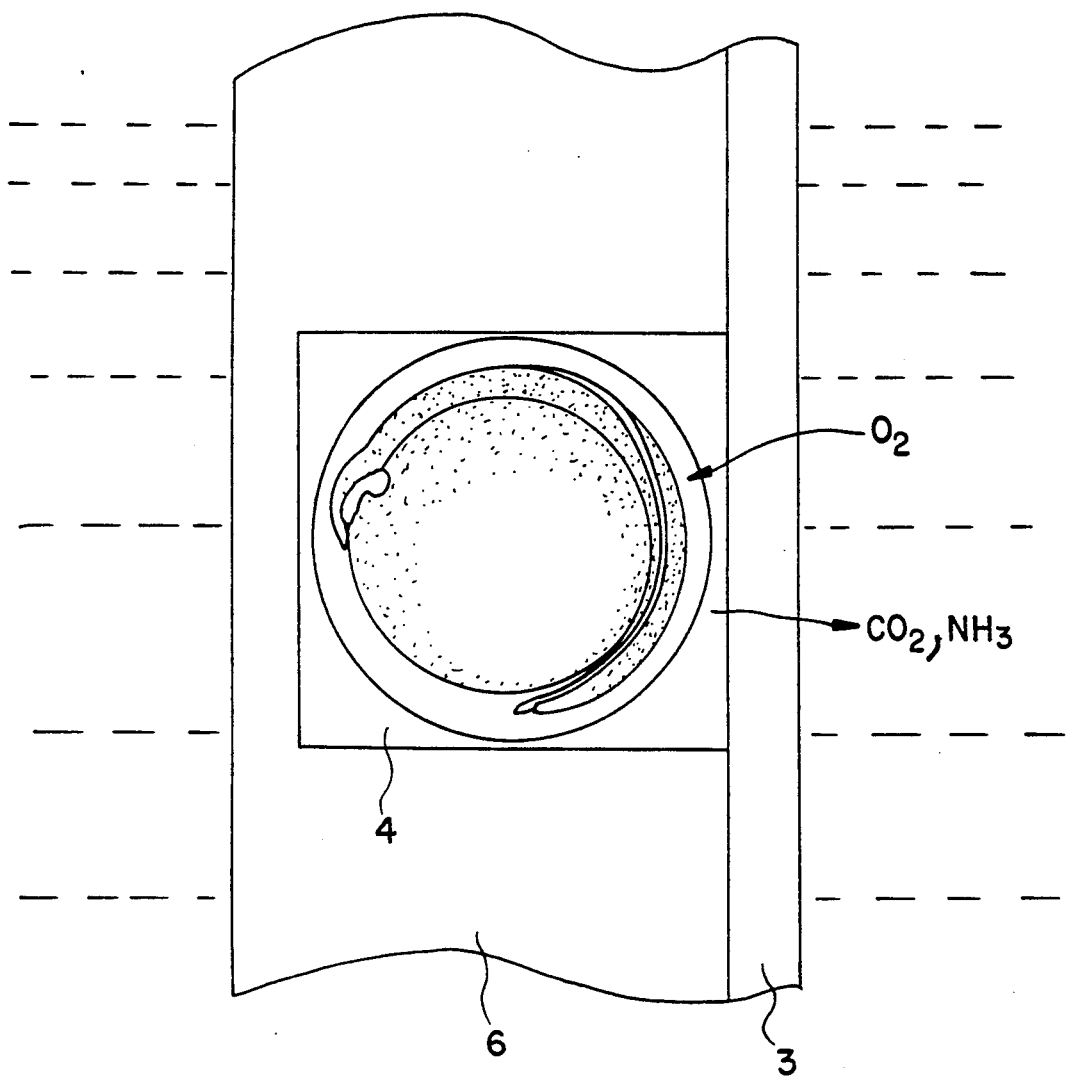
FIG. 4 shows a plan view of a gel chamber in accordance with FIG. 1, illustrating the principles of mass transfer via a membrane.

One mode of carrying out this water distribution is to completely submerge the plates 13 in water, as shown in FIG. 4, where oxygen dissolved in the water passes to the eggs through membrane 3 and waste products $NH_3$ and $CO_2$ pass out through the membrane. However, it is also possible to spray/shower the individual plates with water, thereby providing a downwards flowing water film for allowing mass transfer to occur. When using spray/shower water distribution, the plates should be arranged in a vertical manner.

The typical flow of water through such a case is from about 0.5 to about 1.0 liters/minute with the water having a temperature between about 5 and about 9° C., depending on the species. Sporadic measurements of dissolved oxygen in the water should indicate that water saturated with oxygen prevails.

The incubation procedure is continued for a certain period of time until the eggs are hatched, and the larvae have become viable, e.g. from 6 to 10 weeks in the case of salmon eggs. Then the hatched larvae are simply liberated from the incubation plates by removing the fixing arrangement (e.g. screws) and removing the gel membrane. The larvae may then be transferred to, for example, rearing tanks for start-feeding.

In certain instances, the gel plates will be incubated in a water saturated air atmosphere in the cases described or in larger cases, with or without spraying the plates with water. This spraying can be carried out continuously or periodically. The advantage of this method of incubation is that the water consumption is decreased. Moreover, one has the opportunity to increase the supply of oxygen to the eggs/larvae by increasing the partial pressure of oxygen in the atmosphere surrounding the incubation plate.

The principle of showering/spraying the plates with water simplifies long distance transport of the eggs/larvae during incubation. For such purposes the water should be recirculated in order to decrease the volume of water necessary.

Incubating with plates and membranes comprising a dissolvable gel material is carried out in the same manner as with the PAAm gel described above, except for the different methods for production of the gels. Moreover, the Instacryl-L/-H may also be used for production of dissolvable plates and membranes in accordance with the present invention.

Incubating with Spheres

In the following, an example illustrating production of alginate gel spheres for incubating eggs according to the invention is provided.

The alginate raw material may be provided in powder form. Alginate, e.g. Protan LF 10/60 or LF 20/40, is carefully sprinkled little by little into distilled water under continuous agitation. The concentration of alginate is raised to between 1 and 4%, based upon the weight of water. When adding the powdered alginate, it is important to avoid formation of lumps. The water may, if desired, be heated, for example, to a temperature of up to 100° C. The agitation of the mixture is continued until all alginate is dissolved. If NaCl (0.2 moles/liter) is present in the mixture, the resulting gel will achieve a more homogenous structure, but this is not required. Then the homogenous solution of alginate is cooled, typically to a temperature of 5° C., whereupon the eggs for incubation are added to the mixture. The resulting mixture comprising eggs and alginate solution is added dropwise into an aqueous solution of $CaCl_2$ having a concentration of from about 0.1 to about 1.0 moles/liter. This solution of $CaCl_2$ will typically also have a temperature of about 5° C. The gel formation occurs immediately, but the resulting spheres, each containing completely embedded eggs should harden in the solution for a certain period of time depending on the type of alginate and the concentration of $CaCl_2$. The resulting alginate gel spheres containing the eggs are thereafter transferred to a sufficiently sterilized system for incubation, preferably comprising 0.05–0.2 moles $Ca^{2+}$/mole $K^+$.

Figure 3:
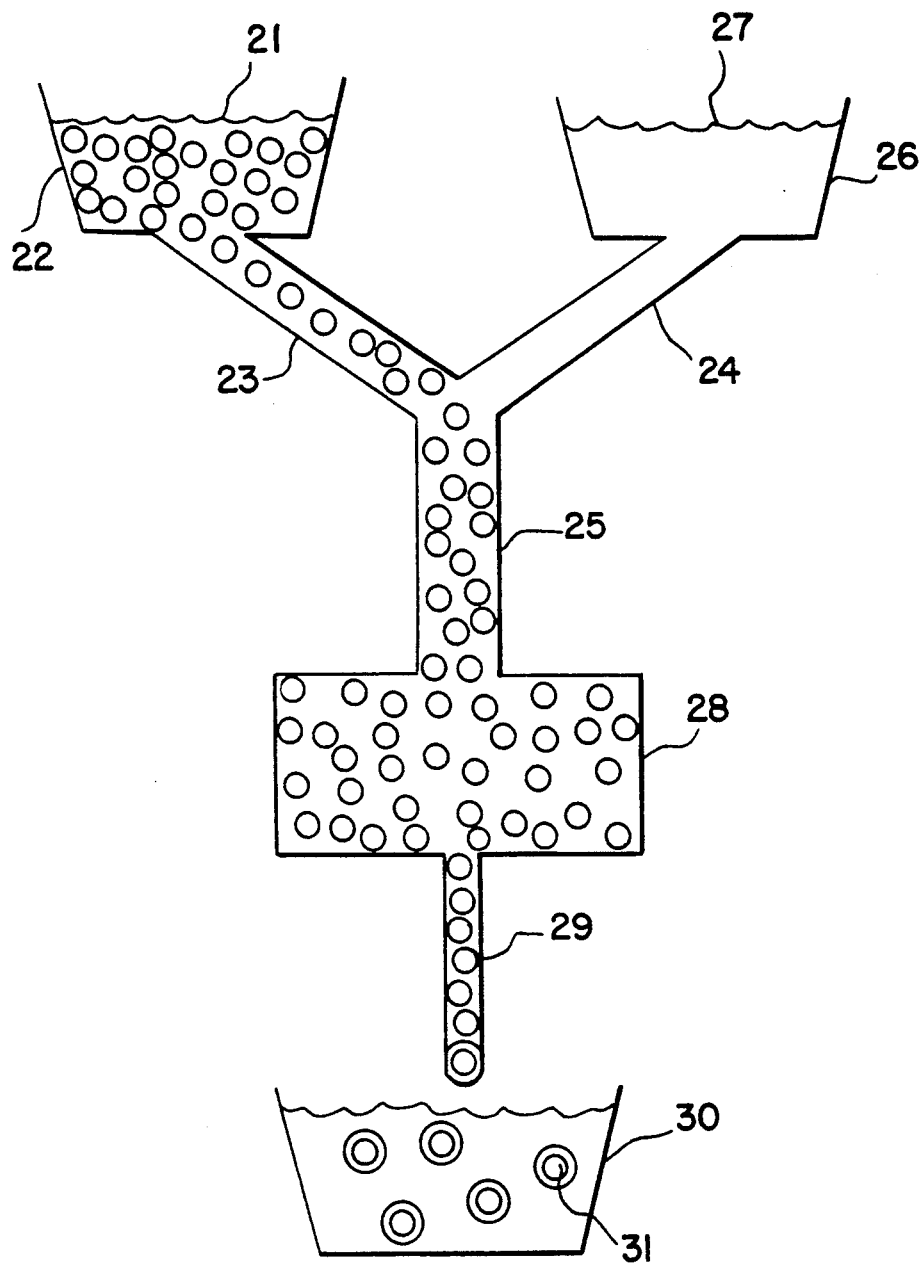
FIG. 3 illustrates one method for encapsulating eggs in a dissolvable gel material.

In FIG. 3, illustrating one method for formation of the spheres, the eggs 21 are supplied to a mixing pipe, hose or the like 25, from a container 22 via a supply pipe 23 and are intermixed with the alginate solution 27 from a second container 26, supplied via a supply pipe 24 or the like. The resulting mixture of eggs and alginate solution is thereafter transferred to a mixing chamber 28, and dropped through a relatively thin tube or the like 29 into a third container 30 containing the solution of $CaCl_2$ 31. Mixing chamber 28 is optional and is not necessary to achieve sufficient mixing.

c) Vaccinating

A customary method for vaccinating fish fry is so-called "dipping or bath vaccination", i.e., the vaccine is not injected, but dissolved in the surrounding water. According to the invention, experiments comprising injection of a vaccine solution into the gel chamber in which the larvae resides, have been carried out. This mode of vaccination has been carried out successfully and the method shows great advantages in that loss of vaccine is negligible. Further, it is possible to carry out an automatic injection of a vaccine solution into the separate chambers, e.g. by using a simple industrial robot. It is also possible to inject the solution directly into the egg yolk in a corresponding manner.

d) Disinfection of Eggs

All the eggs that were utilized in the experiments were disinfected by the supplier by means of Buffodine (100 ppm in 10 minutes). In addition to this treatment, some of the eggs were disinfected in advance of the incubation experiments. However, the results from those experiments do not show any effect on mortality rate of either eggs or larvae from this additional disinfection; since the disinfection by the supplier seems to have been sufficient. On the other hand, those experiments show that the following preparation may be utilized for eggs without any detrimental effects on the eggs:

lysozyme (1 g/liter and 100 ppm, 10–40 min), with the eggs brought into a lysozyme solution before incubation, and in some instances the lysozyme solution poured over the gel plate and down into the individual gel chambers at the same time as supplying the eggs.
Also useful are:
lysozyme (80 ppm) + glycine (1%) for 105 min; Utilized for rainbow trout only.
glutaric aldehyde (Glu) (400 and 800 ppm, 10 min);
Buffodine (100 ppm, 10 min).
Utilized for salmon only.

EXAMPLE 1

This example describes incubation of salmon eggs by means of incubation plates in accordance with the invention, utilizing a continuous flow of water through the incubation system. A total of 30 plates were incubated in the incubation cases. The incubation plates were constructed of PAAm gel or of alginate gel having a width of 14 cm and length of 16 cm, and having a thickness of 1 to 1.5 cm. The plates were rinsed, provided with eggs, and mounted as described above. The complete incubation plates were brought into the incubation cases (each having outer dimensions of 35×19×21 cm), resulting in a total of 6 incubation plates in each case. The incubation lasted from 6 to 10 weeks. The yolk sack larvae remained in the gel for different periods of time after hatching, with a maximum of 3 weeks.

Typical percentage of hatching for the most of the plates was between 88 and 100%. Details concerning the composition of the gels, their dimensions, and the incubation described in Table 2.

TABLE 2

| Plate no. | Days of incubation (Total) | incubation after hatching | Gel (% PAAm) | Membrane | Membrane*) thickness/ pore size | Disinfection | Sterilisation | Percent of hatching | Percent of survival |
|---|---|---|---|---|---|---|---|---|---|
| 1-1#) | 41 | 22 | 15 | Nytran NY 13N | 0.45 μm | | | 93 | 93 |
| 1-6#) | 41 | 22 | 5 | Nytran NY 13N | 0.45 μm | | | 88 | 86 |
| control | 57 | 18 | | | | | | 92 | 98 |
| 4 A | 54 | 15 | 7.5[1)] | Nytran NY 13N | 0.45 μm | | autoclaving | 91 | 50 |
| 4 B | 56 | 17 | 5 | 5% PAAm | 1 mm | lysozym | autoclaving | 92 | 14 |
| 4 C | 90 | 50 | 10 | None (ty11[2)]) | | | | 91 | 71 |
| 4 D | 55 | 18 | 7.5 | Nytran NY 13N | 0.45 μm | lysozym | autoclaving | 83 | 45 |
| 4 E | 51 | 18 | 2[3)] | Two[4)] Nytran | 0.45 μm | | UV-light | 87 | 55 |
| 4 F | 51 | 18 | 7.5[5)] | Nytran NY 13N | 0.45 μm | | autoclaving | 94 | 98 |
| control | 65 | 16 | | | | | | 95 | 100 |
| 6 A | 64 | 15 | 10 | BAS 83[6)] | 0.2 μm | | | 24 | 15 |
| 6 B | 64 | 15 | 10 | BAS 83 | 0.2 μm | Glu | | 39 | 100[7)] |
| 6 C | 65 | 16 | 5 | BAS 83 | 0.2 μm | Glu | | 48 | 77[8)] |
| 6 D | 63 | 15 | 5 | Nytran[9)] | 0.45 μm | | autoclaving | 94 | 93 |
| 6 E | 64 | 16 | 7.5 | 15% PAAm | 0.8 μm | Buff | | 78 | 2 |
| 6 F | 64 | 15 | 5 | 5% PAAm | 1 mm | Buff | autoclaving | 74 | 3 |
| control | 73 | 21 | | | | | | 79 | 100 |
| 7 A | 70 | 18 | 10 | Nytran NY 13N | 0.45 μm | | | 80 | 49 |
| 7 B | 70 | 18 | 10 | 7.5% PAAm | 1.1 mm | | | 83 | 22 |
| 7 C | 70 | 18 | 5 | Nytran NY 13 N | 0.45 μm | Glu | autoclaving | 80 | 100 |
| 7 D | 70 | 18 | 5 | 5% PAAm | 1.5 mm | Glu | autoclaving | 87 | 13 |
| 7 E | 73 | 21 | 7.5 | Nytran NY 13N | 0.45 μm | Buff | autoclaving | 72 | 76 |
| 7 F | 55 | 3 | 7.5 | 5% PAAm | 1 mm | Buff | autoclaving | 78 | 88 |
| control | 36 | 10 | | | | | | 93 | 99 |
| 10 A | 36 | 10 | 7.5 | BAS 83 | 0.2 μm | | autoclaving | 91 | 92 |
| 10 B | 76 | 47 | 10 | None (PVC[2)]) | | | | 85 | 54 |
| 10 C | 30 | 6 | 7.5 | Nucleopore | 8 μm | | autoclaving | 89 | 98 |
| 10 D | 44 | 21 | 7.5 | 5% PAAm | 0.7 mm | | autoclaving | 87 | 13 |
| 10 E | 34 | 9 | 10 | Two[4)] Nytran | 0.45 μm | | | 91 | 86 |
| 10 F | 44 | 22 | 10 | Two[4)] 7.5% PAAm | 0.8 mm | | | 98 | 30 |
| control | 75 | 22 | | | | | | 78 | 99 |
| 11 A | 70 | 17 | 7.5 | Nytran NY 13N | 0.45 μm | | | 86 | 61 |
| 11 B | 70 | 20 | 10 | 5% PAAm | 1 mm | | | 79 | 0 |
| 11 C | 74 | 21 | 7.5 | BA 85 | 0.45 μm | Buff | autoclaving | 91 | 90 |
| 11 D | 74 | 21 | 10 | Nytran NY 13N | 0.45 μm | Buff | autoclaving | 89 | 36 |
| 11 E | 75 | 22 | 10 | Nytran NY 13N | 0.45 μm | Glu | autoclaving | 85 | 22 |

TABLE 2-continued

| Plate no. | Days of incubation (Total) | incubation after hatching | Gel (% PAAm) | Membrane | Membrane*) thickness/ pore size | Disinfection | Sterilisation | Percent of hatching | Percent of survival |
|---|---|---|---|---|---|---|---|---|---|
| 11 F | 70 | 17 | 7.5 | 7.5% PAAm | 1 mm | Glu | autoclaving | 80 | 16 |

Key to Table 2
Buff = Buffodine
Glu = Glutaraldehyde
CB = Chlorine bleach
*)thickness of membrane refers to gel thickness, whereas pore size refers to the membrane filters
incubated in oxygen/air atmosphere
1)Buffodine added to the gel by production of the plate
2)net comprising polyvinyl chloride or tyll (nylon) covering the gel chambers in the gel plate
3)alginate gel plate
4)the chambers made as holes extending through the gel plate, one membrane on each side of the plate
5)open bottom of the gel plate, covered by tyll (nylon)
6)the membrane wetted by sandalwood oil (makes the membrane transparent)
7)18% malformed larvae
8)30% malformed larvae
9)cracks in the membrane

EXAMPLE 2

This example illustrates incubation of eggs from rainbow trout by means of the plates in accordance with the invention, in which, contrary to Example 1, the plates in one incubation case were periodically showered/sprayed, and where one incubation case was provided comprising a water saturated atmosphere without utilizing showering/spraying with water. A total of 41 plates were incubated in the cases spread over a total of 7 cases. The thickness of the gel membranes varied from 1.0 to 1.7 mm.

The incubation lasted for the major part of the plates for 8 to 12 days and the larvae remained in the gel for 0 to 10 days after hatching. Typical percentage of hatching for plates incubated in a continuous flow of water was 80–100%, in which the mortality rate for the larvae after hatching varied from 0–100%. With respect to the plates incubated with periodically spraying/showering with water, the percentage rate of hatching varied from 55 to 90% and the mortality rates from 100–8%. The plate which was sprayed directly exhibited best results. The remaining plates were positioned therebelow, and were wetted with the water from the uppermost positioned plate. This indicates that directly spraying of the plates will stabilize the percentage of hatching and survival at a high level, also in an atmosphere containing air/oxygen.

The advantage of the spraying method is that eggs may be transported in a sealed, sterile system, simplifying control of epidemic diseases and separation of different groups of eggs from each other. Moreover, marine eggs may be transported by airplane with a minimal amount of sea water present.

The plates incubated in a water saturated atmosphere without spraying with water showed, except for one, substantially inferior results with respect to hatching and survival rates than the average for the other series. One plate showed a percentage of hatching of 96% and a survival rate of 91%, and for the remaining five plates, the respective values were 11–71% and zero % (five plates)–11% (one plate), respectively.

This indicates that if it is desired to incubate plates in air/oxygen, the plates should be sprayed periodically or continuously. The reason for this is possibly that spraying/showering is required in order to remove excretory matter.

Further details with respect to this is given in Table 3.

TABLE 3

| Plate no. | Days of incubation (Total) | incubation after hatching | Gel (% PAAm) | Membrane | Membrane*) thickness/ pore size | Disinfection | Sterilisation | Percent of hatching | Percent of survival |
|---|---|---|---|---|---|---|---|---|---|
| #) control | 10 | 6 | | | | | | 92 | 27 |
| 1 A | 10 | 6 | 7.5 | Nytran NY 13N | 0.45 μm | | CB | 98 | 92 |
| 1 B | 10 | 6 | 7.5 | 7.5% PAAm | 1.6 mm | | CB | 70 | 5 |
| 1 C | 8 | 4 | 5 | Nytran NY 13N | 0.45 μm | | CB | 83 | 97 |
| 1 D | 10 | 6 | 5 | 5% PAAm | 0.8 mm | | | 55 | 0 |
| 1 E | 10 | 6 | 7.5 | BAS 83 | 0.2 μm | | | 54 | 0 |
| 1 F. | 10 | 6 | 7.5 | BAS 83 | 0.2 μm | | CB | 74 | 5 |
| ##) control | 13 | 3 | | | | | | 87 | 95 |
| 3 A | 13 | 3 | 5 | BAS 83 | 0.2 μm | | | 93 | 94 |
| 3 B | 13 | 3 | 10 | Nytran NY 13N | 0.45 μm | | CB | 96 | 98 |
| 3 C | 13 | 3 | 7.5 | 7.5% PAAm | 1.0 mm | | CB | 87 | 100 |
| 3 D | 13 | 3 | 7.5 | BAS 83 | 0.2 μm | | CB | 94 | 96 |
| 3 E | 13 | 3 | 10 | Nytran NY 13N | 0.45 μm | | CB | 89 | 100 |
| 3 F | 13 | 3 | 10 | 7.5% PAAm | 0.9 mm | | CB | 94 | 98 |
| ###) control | 10 | 2 | | | | | | 41 | 11 |
| 8 A | 10 | 2 | 7.5 | BA 85 | 0.45 μm | | | 19 | 0 |
| 8 B | 10 | 2 | 10 | BAS 83 | 0.2 μm | | CB | 71 | 0 |
| 8 C | 10 | 2 | 10 | 15% PAAm | 1.5 mm | | CB | 96 | 91 |
| 8 D3) | 9 | 2 | 10 | 7.5% PAAm | 2.7 mm | | UV | 35 | 0 |
| 8 E | 10 | 2 | 5 | BAS 83 | 0.2 μm | | CB | 22 | 0 |
| 8 F | 10 | 2 | 5 | None (PVC2)) | | | CB | 11 | 0 |
| ####) control | 12 | 3 | | | | lysozym | | 94 | 96 |
| 9 A | 12 | 8 | 7.5 | 7.5% PAAm | 2.9 mm | lysozym4) | UV | 76 | 0 |

TABLE 3-continued

| Plate no. | Days of incubation (Total) | incubation after hatching | Gel (% PAAm) | Membrane | Membrane*) thickness/ pore size | Disinfection | Sterilisation | Percent of hatching | Percent of survival |
|---|---|---|---|---|---|---|---|---|---|
| 9 B | 12 | 8 | 5 | Nucleopore | 8 μm | lysozym[4] | | 94 | 59 |
| 9 C | 12 | 10 | 5 | 7.5% PAAm | ? | lysozym[4] | UV | 91 | 50 |
| 9 D | 12 | 7 | 5 | 7.5% PAAm | 1.5 mm | | UV | 87 | 23 |
| 9 E | 11 | 9[5] | 5 | 7.5% PAAm | 0.5 mm | | | 93 | 66 |
| 9 F | 12 | 8[5] | 7.5 | Nucleopore | 8 μm | | UV | 100 | 95 |
| ####) control | 12 | 2 | | | | Glu[6] | | 0[7] | 0 |
| 10 A | 12 | 2 | 7.5 | BA 85 | 0.45 μm | | CB | 100 | 100 |
| 10 B | 8 | 2 | 7.5 | BAS 83 | 0.2 μm | | CB | 66 | 91 |
| 10 C | 2 | — | 7.5 | 7.5% PAAm | 1.7 mm | Glu[8] | CB | 0 | 0 |
| 10 E | 12 | 2 | 10 | BA 85 | 0.45 μm | Glu[6] | CB | 98 | 98 |
| 10 F | 12 | 2 | 7.5 | BAS 83 | 0.2 μm | Glu[6] | CB | 69 | 87 |
| ####) control | 12 | 8 | | | | lysozym + glycin | | 87 | 96 |
| 11 A | 12 | 10 | 10 | 10% PAAm | 1.2 mm | lysozym[4] | | 94 | 6 |
| 11 B | 12 | 8 | 7.5 | 7.5% PAAm | 1.7 mm | | UV | 96 | 78 |
| 11 C | 12 | 7 | 7.5 | 7.5% PAAm | 0.6 mm | lysozym + glycin | UV | 93 | 82 |
| 11 D | 11 | 8 | 5 | 7.5% PAAm | 0.7 mm | | UV | 74 | 8 |
| 11 E | 12 | 9 | 7.5 | 10% PAAm | 0.8 mm | lysozym[4] | | 96 | 33 |
| 11 F | 12 | 9 | 7.5 | 5% PAAm | 2.2 mm | lyso. + glycin[4] | | 96 | 20 |

Key to Table 3
Glu = Glutaraldehye
CB = Chlorine bleach
x) maximum number of days listed: most of the hatching occurred during 2-3 days
ӕ) maximum number of days listed: may vary to some extent within the respective plate (relevant for several plates)
*)thickness of membrane refers to gel thickness, whereas pore size refers to the membrane filters
) case for transportation; incubation in air atmosphere with periodic showering/spraying of the uppermost plate with water. The lowermost plate (in the bottom of the case) was partially submerged in water
) membrane test
) incubated in air saturated with water, without spraying with water
) effect of disinfection
[1]the chambers made as holes extending through the gel plate, one membrane on each side of the plate
[2]net comprising polyvinyl chloride covering the gel chambers in the gel plate
[3]the eggs re-incubated in a new gel plate after four days
[4]lysozyme (+ alternatively glycine) added directly into the gel chambers immediately prior to (and after) formation of the incubation plate system
[5]the plate partly open (damaged) at the bottom, but the chambers covered by tyll (nylon)
[6]glutaric aldehyde (800 ppm, 10 minutes)
[7]the yolk liquid "expanded" out from the eggs after disinfection
[8]glutaric aldehyde (400 ppm, 10 minutes)

EXAMPLE 3

This example illustrates separation of incubated eggs from a stable gel by increasing the gel temperature.

A suspension of marine eggs in a 2% by weight aqueous solution of kappa-carrageenan is maintained at a temperature of 2°-4° C., and added dropwise to a 0.1 molar aqueous KCl solution, also at 2°-4° C. to avoid a temperature shock to the eggs. After a period of a few minutes, the eggs are transferred to a seawater incubation medium at 8° C. containing 0.008 molar K+ which was sufficient to stabilize the gel for a long incubation period at this temperature.

The gel beads were dissolved after incubation by reducing the salinity of the water and carefully raising the temperature to 4°-5° C.

I claim:

1. In a process for incubating live eggs or larvae of fish or crustaceans in an aqueous environment for a predetermined time and at a predetermined temperature to obtain an incubated live organism, the improvement comprising:
    a) protecting said eggs or larvae from mechanical forces and infection by casting, using a mold, a plate of a predetermined shape and dimensions of an aqueous polymeric gel, said plate having at least one depression in a surface thereof for receiving said eggs or larvae, depositing at least one said live egg or larvae in said depression, and covering and sealing said surface and said depression with a porous gas and water permeable membrane;
    b) exposing said plate with covered surface to a source of oxygen and at least intermittent flow of water externally of the membrane for a time and at a temperature sufficient to achieve incubation of said eggs or larvae with passage of oxygen through said membrane to said eggs, and passage of excretory matter through said membrane away from said eggs; and thereafter
    c) removing an incubated live organism from said membrane and plate.

2. A method according to claim 1, wherein the membrane comprises the same aqueous polymeric gel as the plate.

3. A method according to claim 2, wherein the membrane comprises a gel and structural reinforcement.

4. A method according to claim 1 or 2, wherein the aqueous polymeric gel comprises acrylamide, alginate, or kappa-carrageenan.

5. A method according to claim 4, wherein the aqueous polymeric gel comprises alginate, and the plate and membrane are separated from the incubated egg or larva by dissolving the gel.

6. A method according to claim 5, wherein the alginate is maintained as a gel by stabilizing, nontoxic, divalent cations, and dissolved by removing the divalent cations.

7. A method according to claim 1 or 2, wherein the gel is polyacrylamide cross linked with methylene bis-acrylamide.

8. A method according to claim 7, wherein the gel is formed from a solution containing 5-10% by weight acrylamide, and has pores of a diameter 2.4-3.6 nm.

9. A method according to claim 1 or 2, wherein the gel has a water flux of 0.02-1.32 /m$^{-2}$ hour$^{-1}$.

10. A method according to claim 1 or 2, wherein the plate and membrane are immersed in water for the incubation period.

11. A method according to claim or 1 or 2, wherein water is sprayed onto said membrane continuously or intermittently during the incubation period.

12. A method according to claim 1 or 2, wherein depressions are provided in opposite surfaces of said plate, and each of said opposite surfaces is covered and sealed with a membrane.

13. A method according to claim 12, wherein said depressions extend through the entire thickness of said plate.

14. A method according to claim 1 or 2, additionally comprising sterilizing the aqueous polymeric gel prior to depositing said at least one egg or larva.

15. A method according to claim 1 or 2, additionally comprising disinfecting said at least one egg or larva prior to incubating.

16. A method according to claim 1 or 2, additionally comprising vaccinating said at least one egg or larva by injection of a vaccine solution into said at least one depression.

* * * * *